United States Patent [19]
Covain

[11] Patent Number: 5,456,882
[45] Date of Patent: Oct. 10, 1995

[54] REACTION SEGMENT FOR AN AUTOMATIC SAMPLE ANALYZER

[75] Inventor: Serge Covain, Saint-Gely-du-Fesc, France

[73] Assignee: Societe Alcyon Analyzer S.A., Mauguio Cedex, France

[21] Appl. No.: 910,129

[22] PCT Filed: Nov. 13, 1991

[86] PCT No.: PCT/FR91/00897

§ 371 Date: Aug. 31, 1992

§ 102(e) Date: Aug. 31, 1992

[87] PCT Pub. No.: WO92/08987

PCT Pub. Date: May 29, 1992

[30] Foreign Application Priority Data

Nov. 16, 1990 [FR] France .................................. 90 14348

[51] Int. Cl.$^6$ .............................. B01L 3/00; G01N 35/02
[52] U.S. Cl. ............................. 422/64; 422/58; 422/63; 422/100; 422/104; 436/43; 436/47; 436/48
[58] Field of Search ................................. 422/63, 64, 65, 422/67, 68.1, 72, 102, 104, 58; 436/43, 48, 45, 47

[56] References Cited

U.S. PATENT DOCUMENTS

| | | | |
|---|---|---|---|
| 3,882,619 | 5/1975 | Durand et al. ............................ | 40/310 |
| 4,287,155 | 9/1981 | Tersteeg et al. .......................... | 422/64 |
| 4,478,095 | 10/1984 | Bradley et al. ......................... | 422/64 X |
| 4,699,766 | 10/1987 | Yamashita ............................... | 422/64 |
| 4,795,710 | 1/1989 | Muszak et al. .......................... | 435/287 |
| 4,844,868 | 7/1989 | Rokugawa ............................... | 422/64 |
| 4,855,110 | 8/1989 | Marker et al. .......................... | 422/102 |
| 4,900,513 | 2/1990 | Barker et al. ........................... | 422/64 |
| 4,908,320 | 3/1990 | Zakowski et al. ....................... | 436/45 |
| 4,919,887 | 4/1990 | Wakatake ............................... | 422/67 |
| 4,956,148 | 9/1990 | Grandone ................................ | 422/64 |
| 4,961,906 | 10/1990 | Andersen et al. ...................... | 422/102 |
| 4,965,049 | 10/1990 | Lillig et al. ............................ | 422/68.1 |
| 5,051,238 | 9/1991 | Umetsu et al. .......................... | 422/64 |
| 5,084,242 | 1/1992 | Sakuma et al. .......................... | 422/100 |

FOREIGN PATENT DOCUMENTS

| | | |
|---|---|---|
| 0109922 | 5/1984 | European Pat. Off. . |
| 0369840 | 5/1990 | European Pat. Off. . |
| 2142746 | 2/1973 | France . |
| 8800706 | 1/1988 | WIPO . |

*Primary Examiner*—James C. Housel
*Assistant Examiner*—Harold Y. Pyon
*Attorney, Agent, or Firm*—Sandler, Greenblum & Bernstein

[57] ABSTRACT

Reaction segment for a colorimetric analyzer is removably mounted on a revolving plate of the analyzer so that the reaction vessels of the segment are brought one after the other into contact with a measuring device of the analyzer. The segment consists of transparent vertical reaction vessels which are rigidly fixed to a horizontal bar having connected thereto a horizontal plate to which is affixed a device for positioning and guiding into loading and unloading devices of the analyzer and into the opening of the revolving plate.

15 Claims, 5 Drawing Sheets

REACTION SEGMENT FOR AN AUTOMATIC SAMPLE ANALYZER

BACKGROUND OF THE INVENTION

1. Field of the Invention

The present invention is related to a reaction segment for an automatic colorimetric sample analyzer and an analyzer equipped with such a segment.

2. Discussion of Background Information

Currently known analyzers are equipped with reaction vessels in each of which a quantity of blood is mixed, in a measured manner, with a quantity of reagent in order to perform a colorimetric analysis.

After use, these vessels are disposed of.

Some known analyzers are equipped with a fixed plate for receiving the vessels and an analyzer that is mobile with respect to such plate and such vessels.

Other known analyzers are equipped with a fixed colorimetric analyzer, the vessels being mounted on a plate that is mobile with respect to such analyzer.

The present invention is preferably related to a reaction segment adapted to be mounted on a plate that is mobile with respect to the analyzer which can, for example, be the one described in the French Patent Application No. 90 14681, which is the convention application of PCT/FR91/00898 and concurrently filed U.S. patent application Ser. No. 07/849,434.

The advantage procured by the use of a reaction segment with respect to a reaction ring is known.

A reaction segment especially enables much greater flexibility of use.

As a matter of fact, after analyzing the content of the vessels that it comprises, it can be removed easily from the revolving plate without it being necessary to interrupt the operation of the analyzer whereas the replacement of a reaction ring necessitates stopping this device, which engenders a loss of time.

Although the analyzer has a high degree of automation, the reaction segments are still introduced and removed from heir support plate manually.

SUMMARY OF THE INVENTION

The present invention is related to a new type of reaction segment, which can be positioned or removed automatically by equipping the analyzer with loading and unloading devices.

To this end, the reaction segment for an automatic colorimetric sample analyzer adapted to be removably mounted on a revolving plate of the analyzer is such that the reaction vessels of the segment are brought one after the other into contact with a colorimetric analyzer device. The reaction segment comprises reaction vessel 3 that are vertical, spaced uniformly along an arc of a circumference of a circle and affixed to a same horizontal bar 4 shaped like a ring sector. The bar develops from the concave side of the segment and its median zone is extended radially from the concave side of the segment by a horizontal plate 5. At the end of the horizontal plate 5 is fixed a device 6 for positioning and guiding into loading 7 and unloading 8 devices equipping the analyzer, and into an opening 9 present in revolving plate 3.

According to the another characteristic of the invention, the device 6 for positioning and guiding comprises two opposing parallel vertical grooves 10 each having a triangular cross section.

According to yet another characteristic of the invention the guiding and positioning device includes a vertical wall 11 having a square or rectangular shape, at the large front surface 11a of which two vertical walls 12 are fixed, extending in an oblique manner with respect to the rectangular wall. The two oblique walls 12 and the rectangular wall 11 demarcate the vertical grooves 10.

BRIEF DESCRIPTION OF THE DRAWINGS

Other advantages and characteristics of the invention will become more apparent upon reading the description of a preferred embodiment with reference to the annexed drawings in which.

Figure 1:
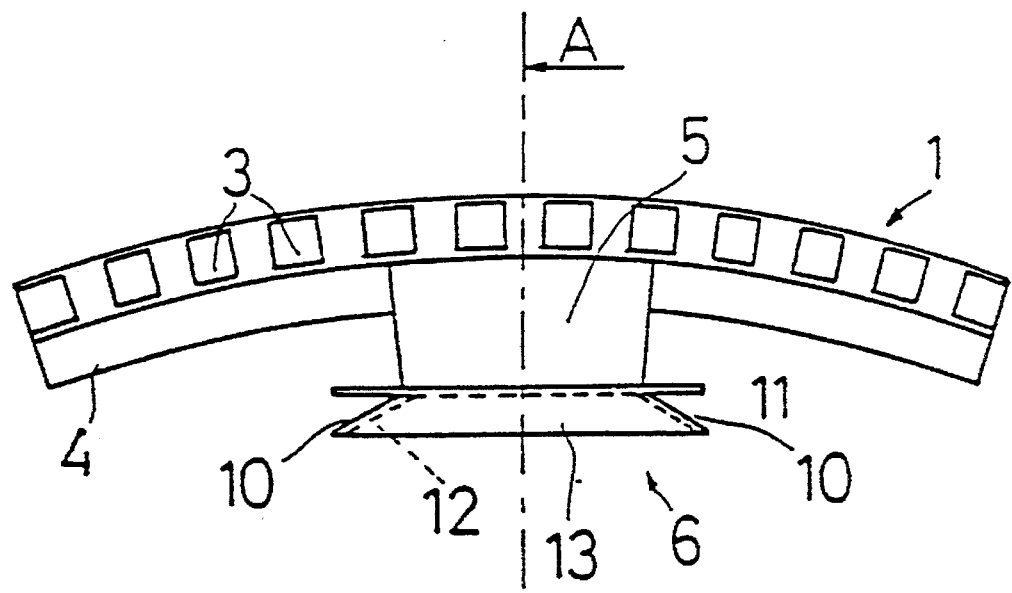
FIG. 1 is a top view of a reaction segment in accordance with the invention.
Figure 2:
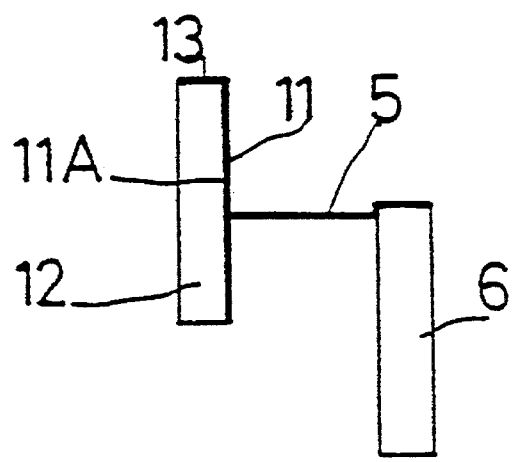
FIG. 2 is a sectional view along line AA of FIG. 1.
Figure 3:
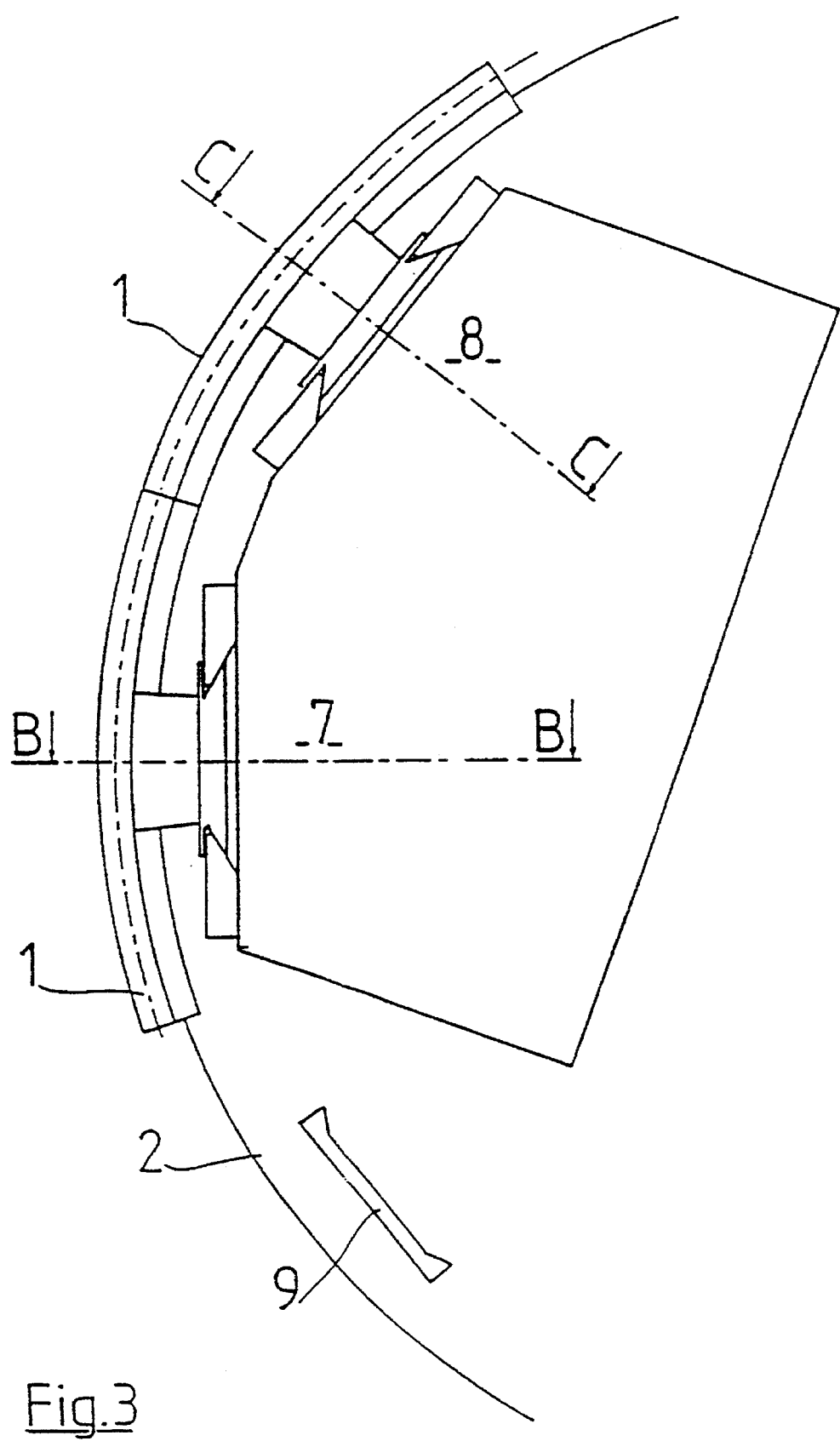
FIG. 3 is a partial top view of an analyzer adapted to receive the segment according to the invention.
Figure 4:
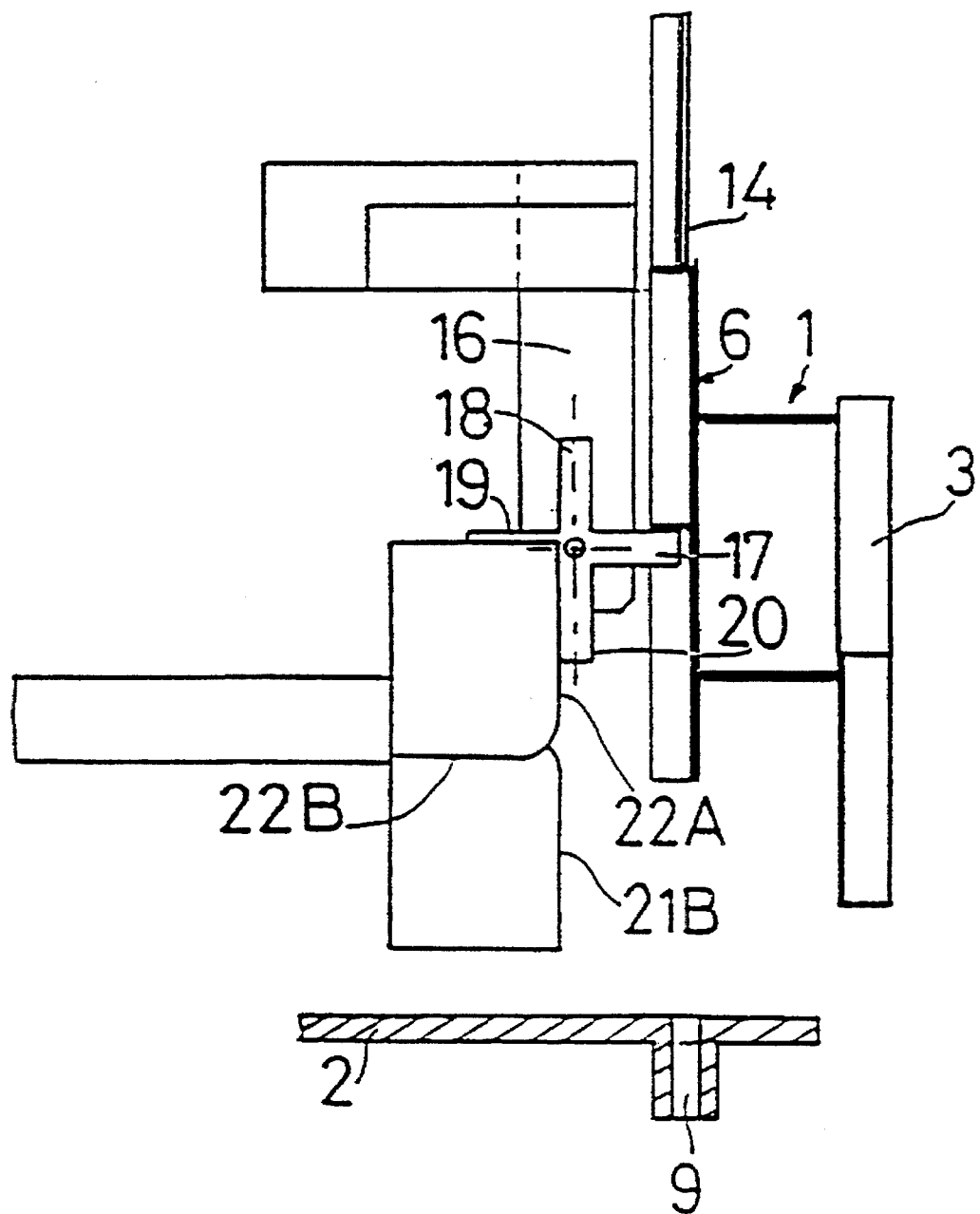
FIG. 4 is a sectional view along line BB of FIG. 3.
Figure 5:
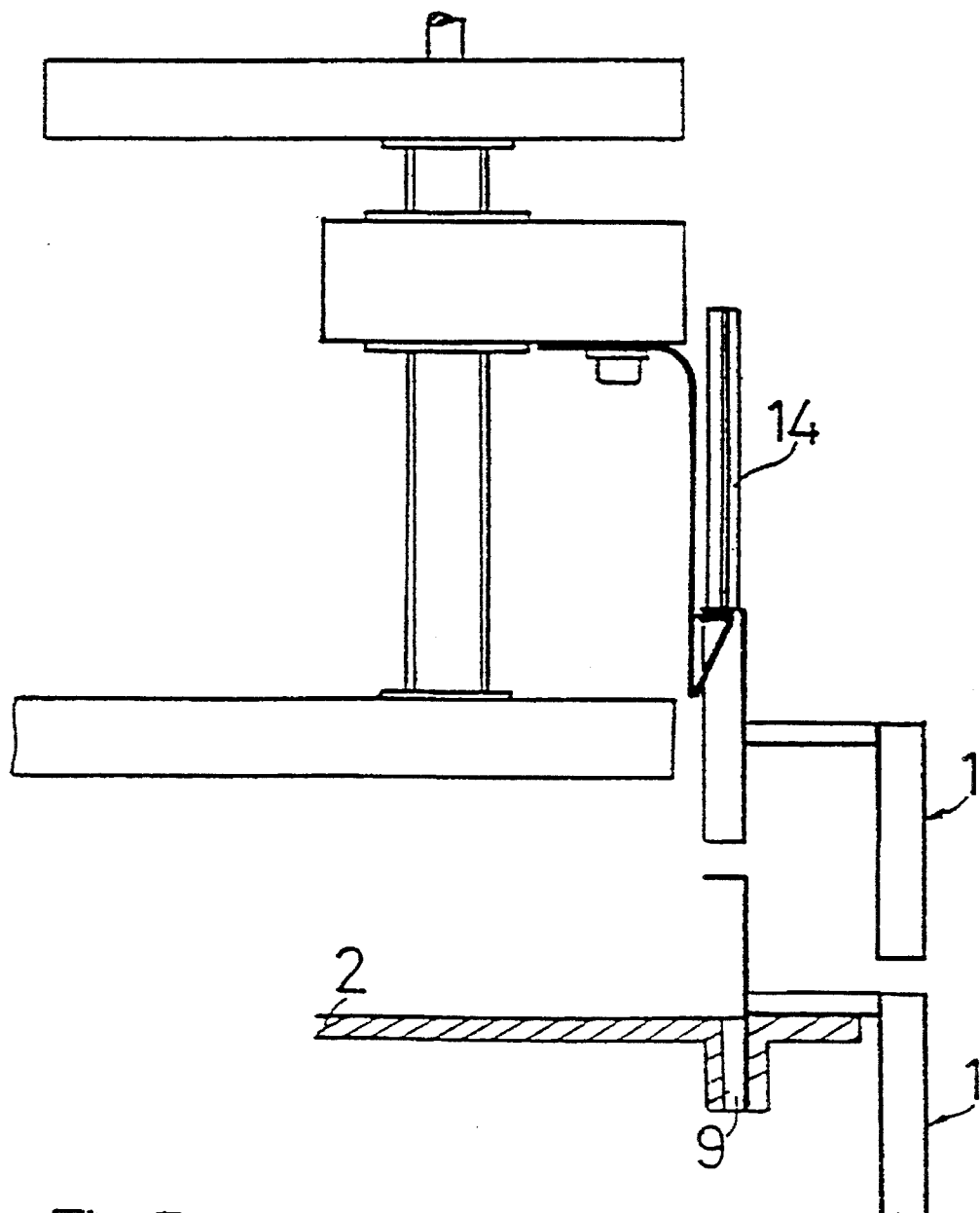
FIG. 5 is a sectional view along line CC of FIG. 3.
Figure 6:
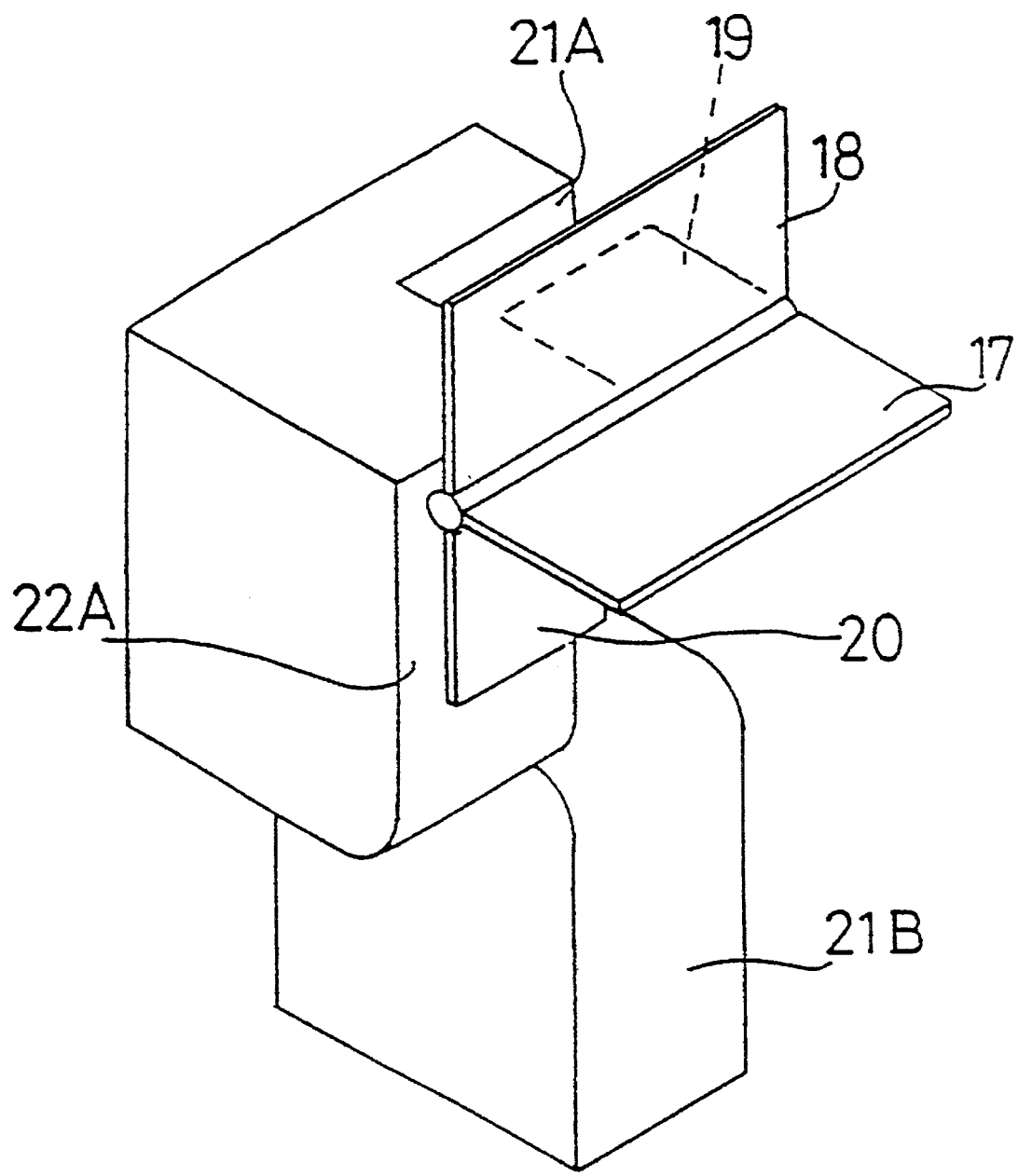
FIG. 6 is a perspective view of the cam of the loading device and the members that cooperate with it.

As represented, the reaction segment 1, as per the invention for an automatic colorimetric sample analyzer adapted to be removably mounted on a revolving plate 2 of the analyzer, comprises a plurality of vertical reaction vessels 3 uniformly spaced along an arc of a circumference of a circle and affixed to a same horizontal bar 4 in the shape of a ring sector, the bar developing from the concave side of the segment and its median zone developing radially from the concave side of the segment by a horizontal plate 5. At the end of the plate fixed a device 6 for positioning and guiding into the loading 7 and unloading 8 devices equipping the analyzer and into an opening 9 present in plate 2.

It must be noted that regular intervals are arranged between vessels 3 of the segment.

DETAILED DESCRIPTION OF THE PREFERRED EMBODIMENTS

Preferably, the vessels are fixed to bar 4 by their upper end.

Yet again in accordance with the preferred embodiment, each vessel has a square cross section.

Still as per the preferred embodiment, means 6 for positioning and guiding comprises two opposing parallel vertical grooves 10 each having a triangular cross section, but it is clear that such grooves can have any other shape.

The device 6 for guiding and positioning is constituted by a vertical wall 11 having a square or rectangular shape, at the large front surface 11a of which two vertical walls 12 are fixed, extending in an oblique manner with respect to the rectangular wall. The two oblique walls 12 and rectangular wall 11 demarcate the two vertical grooves 10.

Preferably the positioning device 6 is developed on either side of the geometrical plane containing the horizontal plate 5.

It is must be noted that the oblique walls, other than demarcating the two grooves 10 with wall 11, constitute with the wall, by virtue of their natural elasticity, a precise positioning and blocking device in the opening 9 of plate 2.

Still as per the preferred embodiment, device 6 of the reaction segment is provided with a horizontal wall 13 joined to the front surface 11a of vertical wall 11 along a portion of the length of the upper edge of wall 11, said wall 13 developing along a horizontal plane that is higher with respect to the horizontal plane along which the upper end of the reaction vessels is developed.

Preferably, the lower horizontal edge of vertical wall 11 of the positioning device is located along a higher level with respect to the lower ends of reaction vessels 3.

It must be noted that when the different reaction segments are stacked one on top of the other, they are in contact with one another by the reaction vessels on the one hand, and by device 6 on the other hand.

Such a reaction segment along with other segments with the same characteristics are adapted to be fixably located on circular plate 2 of the analyzer.

The circular plate is in engagement by an appropriate transmission with the controlled motive member.

Thus, the movement of the plate will be a controlled movement by virtue of which each of the reaction vessels of the segments will be brought in front of the analyzer device.

The circular plate comprises openings 9 at a distance from its perimeter.

As mentioned hereinabove, each opening 9 is adapted to receive in slight blockage, device 6 of one of the reaction segments.

One notes therefore that when reaction segments 1 are positioned on plate 2, they are in support by their horizontal wall 5 on the upper surface of plate 2, the reaction vessels 3 of said segment are perimetric to the plate.

Advantageously, a magazine of non-used segments is attached to loading device 7 of the analyzer, while a second magazine or reception area for used segments 1 is attached to unloading device 8.

According to the preferred embodiment, the first and second stores comprise two vertical guides 14 borne by a frame above the trajectory of the openings of plate 2 and at a distance from said plate. Each guide 14 has a cross-section that has a complementary shape with respect to that of the guide grooves 10 of positioning device 6. The guide grooves cooperating in guidance with guides 14.

The guides thus have a triangular cross section.

The loading device 7 is located at the rear of its store so as to cooperate with device 6 of the lower segment of the segment stack and more specifically with horizontal wall 13 of such segment.

According to the preferred embodiment, the loading device comprises a motive member that activates from top down and base up, along a vertical axis and in synchronization with the rotation of the plate, a mobile equipment comprising a cap 16 in which are rotationally mounted, along a common horizontal axis, a retention element 17, and a thruster element 18 affixed to one another and levers 19 and 20 that cooperate, during the lowering and raising of the mobile equipment one after the other, with a first surface 21 of a fixed cam and with a second surface 22 of the same cam.

According to the preferred embodiment, the retention element 17, the thruster element 18 and the two levers 19 and 20 are fixed to a same hub, rotationally mounted in the cap and extended radially with respect to the hub.

It is must be noted that the element formed by members 17 and 18 and by levers 19 and 20 as well as by the hub is located between the store and the cam.

The retention element and thruster element are perpendicular to one another. The retention and thruster elements include wall having a rectangular shape, the length of this wall is preferably equal to the length of the hub.

The first lever 19 includes a wall of a rectangular shape. The wall is perpendicular to the thruster element and diametrically opposed to the retention element.

It is important to note that this wall 19 only covers half of the length of the hub.

The other lever 20 is diametrically opposed to the thruster element and also includes a rectangular wall.

This rectangular wall is perpendicular to lever 19 and is offset laterally on the hub with respect to the lever 19 so as to only cover the other half of said hub.

The first surface 21 of the cam is adapted to cooperate with lever 19 whereas the second surface 22 cooperates with lever 20.

The first surface 21 has two facets 21A and 21B perpendicular with respect to one another. The first facet 21A is horizontal and comes into contact with lever 19 during the downward movement. The second 21B extends the surface vertically and downwardly.

The second cam surface 22 is adapted to cooperate with the second lever 20 and also has two facets 22A and 22B, the first facet 22A is vertical and comes into contact with lever 20 during the downward movement and is in the same vertical geometrical plane as the second facet 21B. The facet 22B is horizontal and in the same horizontal geometrical plane as facet 21A of the first cam surface.

The functioning of the loading device will now be explained.

In the initial position, the mobile equipment is at the beginning of its downward path and retention element 17 is horizontal and is developed towards the stack of segments located in the store.

The last segment of the stack comes into support against retention element 17 by its wall 13, and the segment stack is immobilized in translation in the store.

As per this initial position, thruster element 18 is vertical and is developed upwardly.

Still in accordance with this initial position, arm 19 is located above surface 21A at a distance from the surface 21A. Lever 20 is in support against surface 22A to oppose any rocking of this assembly about the axis of the hub under the effect of the action exerted by the weight of the segment stack on the retention element.

Still as per the initial position, the axis of the hub will be located along a higher level with respect to the upper portion of surface 22A.

After positioning of one of openings 9 at right angles with the magazine of the loading device, the motive member of the latter will be put into operation and the mobile equipment will begin its downward path.

The movement of the retention element in the downward direction will bring about the movement of the segment stack in the magazine in the direction of opening 9 of the plate.

As long as lever 20 remains in contact with surface 22A, retention element 17 is operative during the downward translational movement.

During this movement, the lower segment of the stack is extracted from its magazine and is conducted towards opening 9 of the plate by two guiding arms affixed to the cap, said guiding arms cooperating with grooves 10 of device 6.

When lever 19 encounters surface 21A, lever 20 has been totally disengaged from surface 22A.

By the combination between the downward movement of the mobile equipment and the support of lever 19 on facet 22A, a pivoting movement about the axis of the hub, from the assembly formed by elements 17, 18, levers 19, 20 and the hub occurs, in conjunction with the downward movement of such assembly.

The pivoting movement of the above defined assembly occurs in a direction corresponding to the angular approach of element 18 towards the reaction segment pile.

Still in the course of this movement, the retention element progressively moves away from the stack and from the segment that it supports.

It must be noted that during this pivoting movement the extraction movement of the lower segment always occurs in the direction of opening 9. At the end or very close to the end of this downward and pivoting movement, the segment has been completely extracted from the magazine and its flange 6. The segment is brought by the guide arms to the level of opening 9 of the plate.

At this stage, element 17 is disengaged from wall 13 and thruster element 18, upon approaching from a horizontal position, comes into support on the upper surface of wall 13. This and this results in device 6 penetrating into opening 9.

At the end of the pivoting movement, the thruster element occupies a horizontal position, lever 19 is in support against facet 21B of surface 21 of the cam and opposes the rear rocking movement of the thruster element. The downward movement continues as long as plate 5 of the segment is not in support against the upper surface of the plate. During this downward movement, the movement of the thruster will be a translational movement.

An end of the path a sensor can be provided, that is activated at the end of the downward path by the mobile equipment. The sensor inverts the energy supply direction of the motive member and triggers the upward movement.

At the end of the downward path, lever 20 is once again located horizontally beneath and at a distance from facet 22B. During the upward movement lever 20 will come into abutment against the facet, resulting in the rearward pivoting about the axis of the hub of the assembly formed by the hub, elements 17 and 18 and levers 19 and 20.

During this rear pivoting and upward movement, the retention element, while approaching from a position close to the horizontal, will come into contact with the lower surface of wall 13 of the last segment of the stack and will lift the entire stack.

It must be noted that the last element of the stack, before being lifted by element 17, is partially extracted from the magazine and comes to rest on the segment that has just been placed on the plate.

The upward movement of element 17 will also have the effect of bringing the last element of the stack back into the store.

During this upward movement, the guide arms will be brought back laterally along guides 14 of the magazine.

The positioning of a segment on the plate by introducing device 6 of the segment in opening 9 of the plate can only be done when wall 13 is placed on the downward trajectory of thruster element 18.

If this wall were to be placed above this trajectory, element 18 would be inoperative, the downward movement of the mobile equipment could continue without producing any results.

Such a situation, wherein wall 13 is above the downward trajectory of element 18 will occur when the segment is either blocked in the magazine or when it comes to bear on the segment that is already positioned and placed unexpectedly in the axis of the magazine.

One can immediately see the advantages of such a solution.

Wall 13 of each segment positioned on the revolving plate is separate from the upper surface of such plate and can cooperate with the unloading device 8. This unloading device includes a motive member activating, along a vertical axis and along a downward and then upward movement and a hooking device of this wall 13 including a hook mounted at the end of an elastically flexible vertical notch.

Preferably, the hooking device will be fixed by an upper end to a plate bearing two guide arms that will come into engagement in grooves 10 of the segment in order to guide it towards guides 14 of the magazine of the unloading device.

In an effort towards simplification, a single motive member can control the movements of the mobile equipment of the loading device and of the hooking device of the unloading device.

It is understood that the present invention can incorporate all arrangements and variations thereof without leaving the scope of the present patent.

What is claimed is:

1. In combination, an automatic colorimetric sample analyzer and reaction segments;

said automatic colorimetric sample analyzer comprising:
a revolving, circular plate defining a perimeter and including a plurality of openings spaced at a distance from said perimeter;
a magazine for stocking non-used reaction segments;
a loading device for reaction segments;
an unloading device for reaction segments; and
said loading device being located at a rear portion of said magazine and cooperating with said non-used reaction segments in said magazine; said loading device comprising a motive member that moves along a vertical axis, said motive member comprising a cap, a retention element and a thruster element attached to one another and rotationally mounted on said cap, and levers rotationally mounted on said cap; and a fixed cam including first and second surfaces, fixed to said motive member so that, during upward and downward movement of said motive member, said levers cooperate
with said first and second surfaces of said cam; and each of said reaction segments adapted to be removably mounted in said revolving plate, and comprising:
a plurality of vertical reaction vessels uniformly spaced along an arc of a circumference of a circle each defining an inner concave side;
a horizontal bar affixed to each said inner concave side;
a horizontal plate extending from said inner concave side; and
means fixed to said horizontal plate for positioning and guiding said reaction segments into the loading and unloading devices and into said plurality of openings in said revolving plate.

2. The combination of claim 1, wherein said means for positioning and guiding extend on either side of a plane passing through said horizontal plate.

3. The combination of claim 1, wherein said reaction vessels have a square cross-section.

4. The combination of claim 1, wherein said horizontal plate extends from a median portion of said horizontal bar.

5. The combination of claim 1, wherein said horizontal plate includes at least one end and said means for positioning and guiding is fixed at said at least one end.

6. The combination of claim 1, wherein said means for positioning and guiding comprise two opposite parallel vertical grooves and said magazine comprises two vertical guides above said openings of said plate and separate from said plate, said guides comprise a cross-section of a complementary shape of said grooves for guiding said positioning means and said grooves cooperate with said vertical guides.

7. The combination of claim 1, wherein said revolving plate comprises an upper surface and said reaction segments are supported on said upper surface of said revolving plate by said horizontal wall.

8. The combination of claim 1, wherein the automatic colorimetric sample analyzer further comprises a magazine for stocking used reaction segments.

9. The combination of claim 8, wherein said means for positioning and guiding comprise two opposite parallel vertical grooves and said magazine comprises two vertical guides above said openings of said plate and separate from said plate, said guides comprise a cross section of a complementary shape of said grooves for guiding said positioning means and said grooves cooperate with said vertical guides.

10. The combination of claim 1, wherein said means for positioning and guiding comprise two opposite parallel vertical grooves.

11. The combination of claim 10, wherein said two opposite parallel vertical grooves have a triangular cross-section.

12. The combination of claim 11, wherein said means for positioning and guiding further comprise a first vertical wall and two vertical, oblique walls affixed to said first vertical wall; wherein said first vertical wall and said oblique walls define said vertical grooves.

13. The combination of claim 12, wherein said first vertical wall defines a square or rectangularly shaped front surface.

14. The combination of claim 13, wherein said reaction vessels comprise an upper end and said first vertical wall includes an upper edge; and said means for positioning and guiding include a horizontal wall attached to said front surface of said first vertical wall along a portion of said upper edge of said vertical wall and said horizontal wall is higher than said upper end of said reaction vessels.

15. The combination of claim 13, wherein said reaction vessels comprise a lower end and said first vertical wall includes a lower edge; and said lower edge of said first vertical wall is higher than said lower end of said reaction vessels.

* * * * *